(12) United States Patent
Taniguchi et al.

(10) Patent No.: US 11,612,312 B2
(45) Date of Patent: Mar. 28, 2023

(54) INTUBATION SYSTEM

(71) Applicant: NIHON KOHDEN CORPORATION, Tokyo (JP)

(72) Inventors: Yukio Taniguchi, Tokorozawa (JP); Tsutomu Wakabayashi, Tokorozawa (JP); Fumihiko Murayama, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 1005 days.

(21) Appl. No.: 16/366,151

(22) Filed: Mar. 27, 2019

(65) Prior Publication Data
US 2019/0298952 A1  Oct. 3, 2019

(30) Foreign Application Priority Data

Mar. 28, 2018  (JP) ................................. 2018-062120

(51) Int. Cl.
*A61B 1/00* (2006.01)
*A61B 1/267* (2006.01)
(Continued)

(52) U.S. Cl.
CPC ............ *A61B 1/267* (2013.01); *A61B 1/0002* (2013.01); *A61B 1/00009* (2013.01);
(Continued)

(58) Field of Classification Search
CPC .......... A61M 16/0488; A61M 2205/18; A61M 2205/3313; A61M 2205/3375;
(Continued)

(56) References Cited

U.S. PATENT DOCUMENTS 5,701,904 A * 12/1997 Simmons ............. A61B 3/1208
600/358
7,946,981 B1 * 5/2011 Cubb ................. A61B 1/00103
600/187
(Continued)

FOREIGN PATENT DOCUMENTS

JP     2007-144123 A    6/2007
JP     2011-036372 A    2/2011
(Continued)

OTHER PUBLICATIONS

Japanese Office Action dated Nov. 16, 2021 issued in Japanese Patent Application No. 2018-062120.

*Primary Examiner* — Timothy J Neal
*Assistant Examiner* — Sung Ham
(74) *Attorney, Agent, or Firm* — Pearne & Gordon LLP (57) ABSTRACT

An intubation system includes a measurement apparatus that measures physiological parameter of a subject by a measuring section, an intubation apparatus that includes an imaging section placed in a vicinity of a tip end portion of an inserting section to be inserted from a mouth of the subject toward a target site, an intubation displaying section that is disposed integrally with or separately from the intubation apparatus and is connected to the imaging section and the measuring section to display an in vivo image that is taken by the imaging section along with the physiological parameter that is measured by the measuring section, and an overall storage section that stores the in vivo image and physiological parameter that are displayed on the intubation displaying section, in an associated manner.

9 Claims, 7 Drawing Sheets

(51) Int. Cl.
*A61M 16/04* (2006.01)
*A61B 5/1455* (2006.01)
*A61B 5/00* (2006.01)
*A61B 5/0205* (2006.01)
*A61B 5/024* (2006.01)

(52) U.S. Cl.
CPC ...... *A61B 1/00052* (2013.01); *A61B 1/00097* (2022.02); *A61B 5/0205* (2013.01); *A61B 5/14551* (2013.01); *A61B 5/743* (2013.01); *A61M 16/0488* (2013.01); *A61B 5/024* (2013.01)

(58) Field of Classification Search
CPC .. A61M 2205/3569; A61M 2205/3592; A61M 2205/505; A61M 2205/52; A61M 2205/581; A61M 2205/582; A61M 2205/583; A61M 2205/6063; A61M 2230/06; A61M 2230/205; A61B 1/0002; A61B 1/00052; A61B 1/04; A61B 1/267; A61B 5/0205; A61B 5/14551; A61B 5/743; A61B 5/024; A61B 1/00009; A61B 1/0005; A61B 5/0084
USPC .......................................................... 600/120
See application file for complete search history.

(56) References Cited

U.S. PATENT DOCUMENTS

| | | | |
|---|---|---|---|
| 2007/0106117 A1* | 5/2007 | Yokota | H04N 5/232945 348/E5.025 |
| 2007/0106122 A1 | 5/2007 | Yokota et al. | |
| 2011/0263935 A1* | 10/2011 | Qiu | A61B 1/00009 382/128 |
| 2015/0080655 A1* | 3/2015 | Peterson | A61B 1/00011 600/112 |
| 2015/0272423 A1 | 10/2015 | Ito et al. | |
| 2016/0095506 A1* | 4/2016 | Dan | A61B 1/0005 600/188 |
| 2017/0291001 A1* | 10/2017 | Rosenblatt | G16H 30/40 |
| 2018/0221610 A1* | 8/2018 | Larson | A61B 1/0684 |
| 2018/0353160 A1* | 12/2018 | Oura | G16H 30/20 |
| 2019/0133430 A1* | 5/2019 | Inglis | A61B 1/00016 |
| 2019/0224434 A1* | 7/2019 | Silver | A61H 31/00 |
| 2020/0170498 A1 | 6/2020 | Galloway et al. | |

FOREIGN PATENT DOCUMENTS

| | | |
|---|---|---|
| JP | 2011036372 A * | 2/2011 |
| JP | 2013-085880 A | 5/2013 |
| WO | 2014-156378 A1 | 10/2014 |
| WO | 2017-151796 A1 | 9/2017 |

* cited by examiner

INTUBATION SYSTEM

CROSS REFERENCE TO RELATED APPLICATION

This application is based on Japanese Patent Application No. 2018-062120 filed on Mar. 28, 2018, the contents of which are incorporated herein by reference.

BACKGROUND

The present invention relates to an intubation system, and particularly to an intubation system having an intubation apparatus which inserts an intubation tube into a target site along an inserting section that is inserted through the mouth of a subject.

In an intubation into a target site such as the trachea, conventionally, an intubation tube is inserted toward the target site while spreading the larynx with a laryngoscope which is inserted through the mouth of the subject, and directly viewing the target site from the outside. However, it is difficult to clearly view the target site and a tip end portion of the intubation tube from the outside, and there is a possibility that the intubation tube may not be smoothly inserted into the target site.

As a technique for enabling a target site and a tip end portion of an intubation tube to be clearly viewed, for example, JP-A-2007-144123 proposes an intubation support apparatus which exhibits operability in the case where an insertion tool is inserted into the trachea of a patient.

When the intubation support apparatus is used, an image of an observation site where the tip end of the insertion tool exists is taken by imaging means, and the taken image is displayed on a displaying section. Therefore, the trachea and the tip end portion of the intubation tube can be clearly seen through the image.

Here, there is a case where an intubation apparatus is operated while checking physiological parameter of the subject which is measured by measurement apparatuses such as a patient monitor, a defibrillator, and a respirator. In the intubation support apparatus of JP-A-2007-144123, in such a case, the user is required to shift the gaze from the displaying section on which an in vivo image is displayed, to check physiological parameter measured by the measurement apparatuses, and therefore it is difficult to easily know a plurality of sets of intubation information relating to intubation such as the in vivo image and physiological parameter.

The invention has been conducted in order to solve the problem in the prior art. It is an object of the invention to provide an intubation system in which a plurality of sets of intubation information can be easily known.

SUMMARY OF THE INVENTION (1) According to an aspect of the invention, an intubation system includes a measurement apparatus that measures physiological parameter of a subject by a measuring section, an intubation apparatus that includes an imaging section placed in a vicinity of a tip end portion of an inserting section to be inserted from a mouth of the subject toward a target site, an intubation displaying section that is disposed integrally with or separately from the intubation apparatus and is connected to the imaging section and the measuring section to display an in vivo image that is taken by the imaging section along with the physiological parameter that is measured by the measuring section, and an overall storage section that stores the in vivo image and physiological parameter that are displayed on the intubation displaying section, in an associated manner.

(2) In the intubation system (1), the displaying section displays a composite image obtained by synthesizing the physiological parameter with the in vivo image, and the overall storage section stores the composite image.

(3) The intubation system (1) or (2) further includes a storage controller that controls a start timing of storing the in vivo image that is taken by the imaging section and the physiological parameter that is measured by the measuring section, in the overall storage section based on at least one of the in vivo image and the physiological parameter.

(4) In the intubation system (3), the intubation apparatus includes a detecting section that detects a target site, from the in vivo image that is taken by the imaging section, based on a feature amount of the target site that is preset, and an intubation determining section that determines whether an intubation tube is insertable into the target site or not, based on a position of the target site which is detected by the detecting section, and an advancing direction of the intubation tube which is disposed so as to be advanceable and retractable along the inserting section. In the system, when the intubation determining section determines that the intubation tube is insertable into the target site, the storage controller causes the overall storage section to start storing the in vivo image and the physiological parameter.

(5) The intubation system of any one of (1) to (4) further includes at least one of:
  a vibrating section of the intubation apparatus that vibrates a grasping portion of the intubation apparatus to be grasped by an operator; and
  a sound outputting section that outputs a warning sound in the measuring section; and
  a notification controller that causes at least one of the vibrating section and the sound outputting section to operate when a value of the physiological parameter that is measured by the measuring section reaches a given threshold.

(6) In the intubation system of any one of (1) to (5), the overall storage section is disposed in the measurement apparatus, the measurement apparatus includes a measurement displaying section that displays the physiological parameter that is measured by the measuring section, and displays the in vivo image stored in the overall storage section together with corresponding physiological parameter on the measurement displaying section.

According to the presently disclosed subject matter, the intubation displaying section displays the physiological parameter that is measured by the measuring section together with the in vivo image that is taken by the imaging section, and the overall storage section stores the in vivo image and physiological parameter that are displayed on the intubation displaying section, in an associated manner. Therefore, it is possible to provide an intubation system in which a plurality of sets of intubation information can be easily known.

DETAILED DESCRIPTION OF EMBODIMENTS

Hereinafter, embodiments of the presently disclosed subject matter will be described with reference to the accompanying drawings.

Embodiment 1

Figure 1:
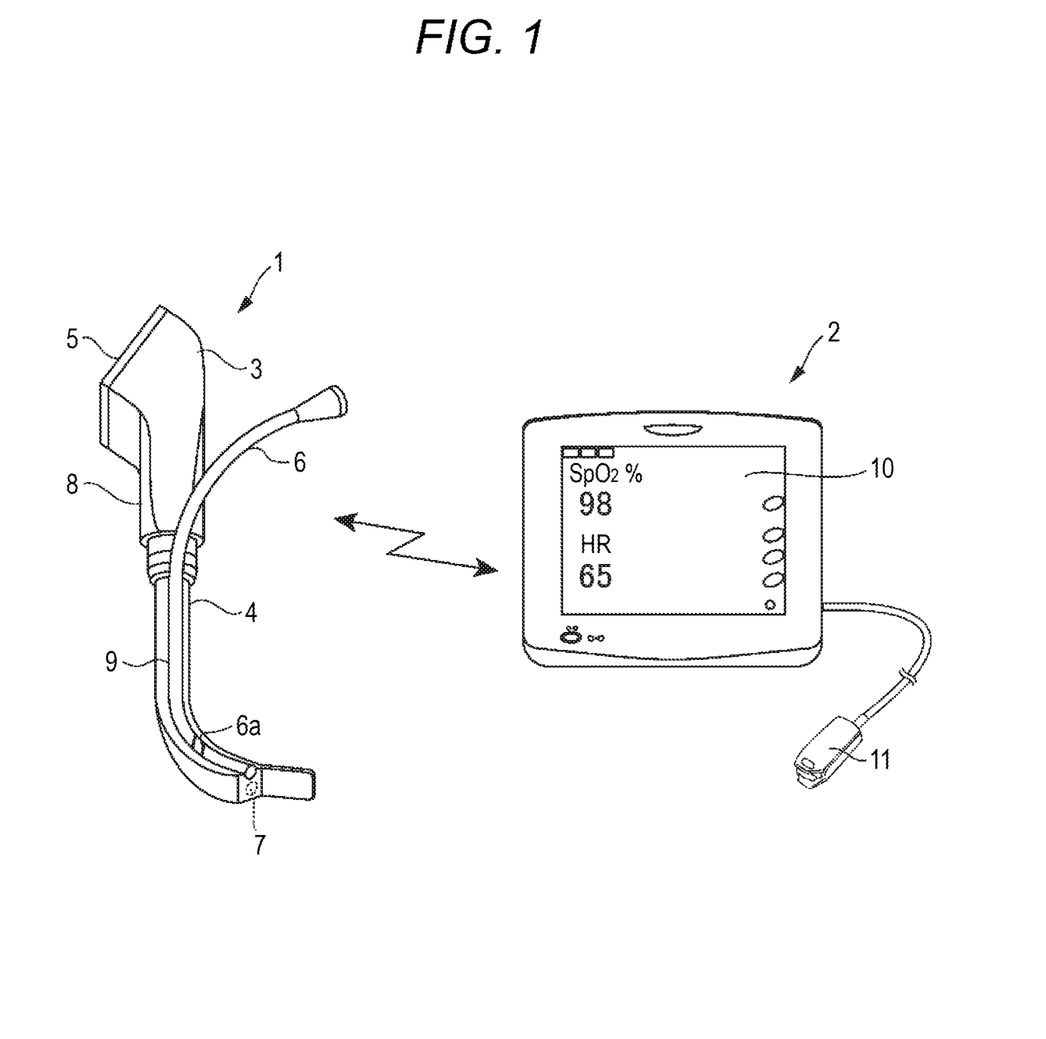
FIG. 1 is a view illustrating the configuration of an intubation system of Embodiment 1 of the presently disclosed subject matter.

FIG. 1 illustrates the configuration of an intubation system of Embodiment 1 of the presently disclosed subject matter. The intubation system may include an intubation apparatus 1 and a measurement apparatus 2.

The intubation apparatus 1 may include an apparatus body 3. An inserting section 4 is detachably attached to a lower portion of the apparatus body 3, and an intubation displaying section 5 is disposed in an upper portion of the apparatus body 3. An intubation tube 6 is placed along a side portion of the inserting section 4, and an imaging section 7 is placed in the vicinity of a tip end portion of the inserting section 4.

The operator operates the apparatus body 3 to perform intubation. A grasping portion 8 is formed in the lower half portion of the apparatus body 3. In order to allow the operator to easily grasp the grasping portion 8, the grasping portion has a size which enables the portion to fit in the hand of the operator, and is formed into a columnar shape.

The inserting section 4 is to be inserted from the mouth of the subject toward the glottis, has an elongated shape, and is formed so that the tip end side is arcuated. A groove portion 9 which elongates from the basal end portion to the tip end portion is formed in the side portion of the inserting section 4. The groove portion 9 holds the intubation tube 6 in an advanceable and retractable manner, and is formed so as to have a size which corresponds to the intubation tube 6.

The intubation tube 6 has a tubular shape, and is formed so as to elongate along the groove portion 9 of the inserting section 4. Here, the intubation tube 6 is placed in the groove portion 9 in a manner that the tube is advanceable into and retractable from the tip end portion of the inserting section 4, and can be advanced in a predetermined advancing direction while being restricted by the groove portion 9. An insertion mark 6a which functions as a guide in the case where the intubation tube 6 is to be inserted through the glottis is formed in the vicinity of the tip end portion of the intubation tube 6.

The imaging section 7 takes an in vivo image of the subject, and is placed so as to be forwardly directed in the vicinity of the tip end portion of the inserting section 4. Namely, the imaging section is placed so as to be directed in a direction along which an extension of the inserting section 4 extends. For example, the imaging section 7 may be configured by a CCD image sensor or the like.

The intubation displaying section 5 is connected to the imaging section 7, and displays an in vivo image which is taken by the imaging section 7 in order to enable the operator to operate the inserting section 4 and the intubation tube 6. For example, the intubation displaying section 5 may be configured by a display device such as a liquid crystal display.

The measurement apparatus 2 may include a measurement displaying section 10, and a measuring section 11 is connected to the measurement displaying section 10. Examples of the measurement apparatus 2 are a patient monitor, a defibrillator, and a respirator.

The measuring section 11 measures a physiological parameter of the subject. For example, the physiological parameter is information relating to an intubation. Examples of the physiological parameter are the oxygen saturation ($SpO_2$) and the heart rate. The measuring section 11 may be configured by, for example, an irradiator which irradiates the fingertip or the like of the subject with a light beam, and a light detector which detects a transmission light beam that is transmitted through the fingertip, or a reflection light beam that is reflected from the fingertip. Preferably, the light beam which is emitted from the irradiator has a wavelength of 600 to 1300 nm. For example, the irradiator may emit a red light beams of a wavelength of 660 nm, and an infrared light beam of a wavelength of 940 nm, and the light detector may receive the red and infrared light beams which are transmitted through the fingertip.

The measurement displaying section 10 displays the physiological parameter of the subject which is measured by the measuring section 11. In the same or similar manner as the intubation displaying section 5, the measurement displaying section 10 may be configured by a display device such as a liquid crystal display.

The intubation apparatus 1 and the measurement apparatus 2 are wirelessly connected to each other.

Next, the configurations of the intubation apparatus 1 and the measurement apparatus 2 will be described in detail.

Figure 2:
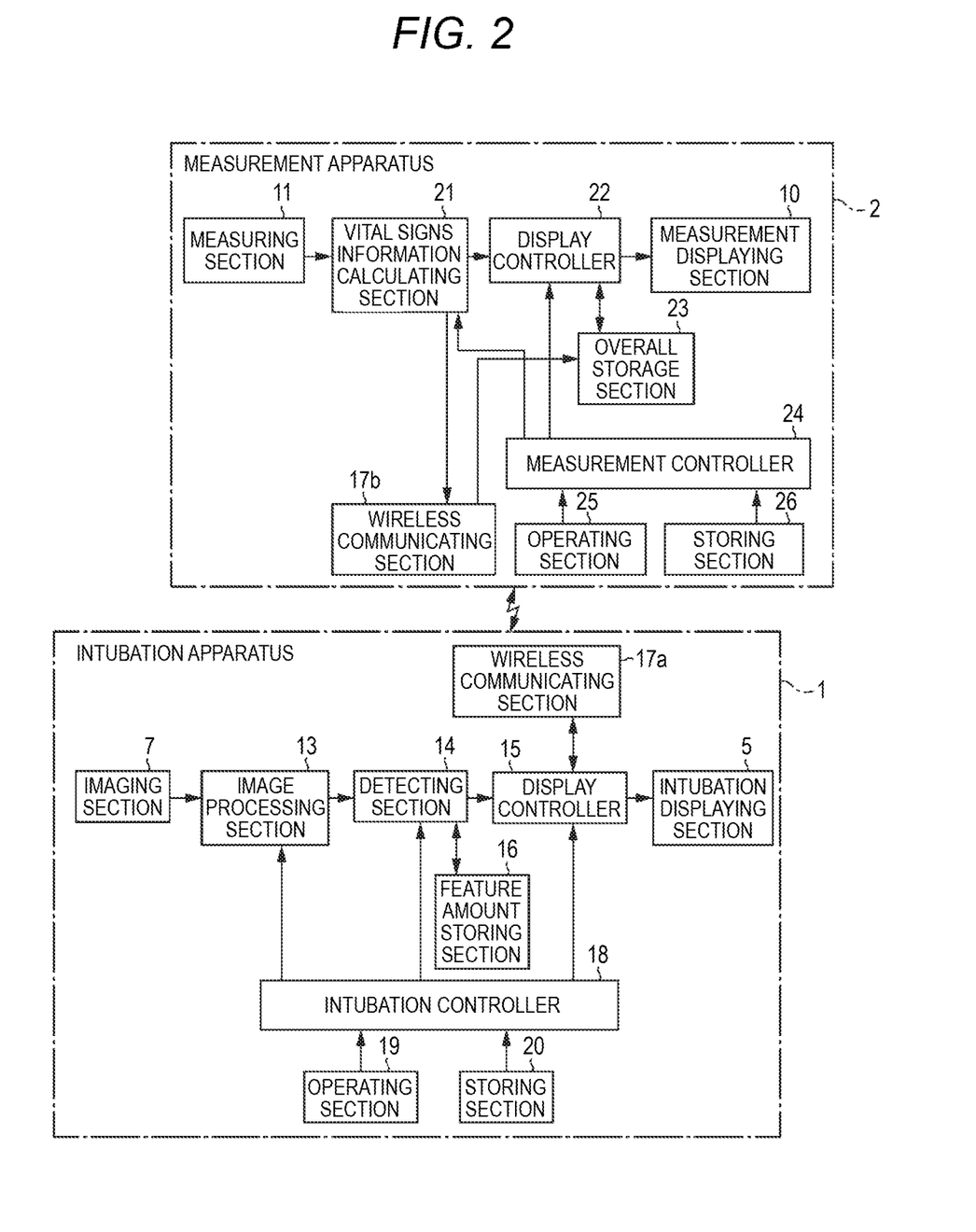
FIG. 2 is a block diagram illustrating the configurations of an intubation apparatus and a measurement apparatus.

As illustrated in FIG. 2, the intubation apparatus 1 may include an image processing section 13 which is connected to the imaging section 7, and a detecting section 14, a display controller 15, and the intubation displaying section 5 are sequentially connected to the image processing section 13. A feature amount storing section 16 is connected to the detecting section 14, and a wireless communicating section 17a is connected to the display controller 15. Furthermore, an intubation controller 18 is connected to the image processing section 13, the detecting section 14, and the display controller 15, and an operating section 19 and a storing section 20 are connected to the intubation controller 18.

The image processing section 13 processes an image signal of the in vivo image which is taken by the imaging section 7, and produces an in vivo image which is to be displayed on the intubation displaying section 5.

The feature amount storing section 16 is configured by a memory, a hard disk drive, or the like, extracts the feature amount of an image of the glottis which is previously taken, and stores the feature amount. Example of the feature amount of the glottis are the shape value of the vocal cords, the chromaticity of the vocal cords, and the like.

The detecting section 14 detects the glottis from the in vivo image which is taken by the imaging section 7, as the target site based on the feature amount of the glottis which is read from the feature amount storing section 16.

The display controller 15 produces a composite image which is obtained by synthesizing the physiological parameter that is measured by the measuring section 11 of the measurement apparatus 2, with the in vivo image that is taken by the imaging section 7, and controls the intubation displaying section 5 so as to display the composite image. The display controller 15 causes a target mark to be displayed on the intubation displaying section 5 at a predetermined position in the advancing direction of the intubation tube 6 with superimposed on the composite image, and a site mark to be displayed on the intubation displaying section 5 at the position of the glottis which is detected by the detecting section 14 with superimposed on the composite image. Here, the advancing direction of the intubation tube 6 is previously set based on the forming direction of the groove portion 9 in the inserting section 4. For example, the advancing direction is set on the extension of the groove portion 9.

The wireless communicating section 17a wirelessly receives physiological parameter which is measured by the measuring section 11 of the measurement apparatus 2, and wirelessly transmits the composite image which is produced by the display controller 15, to the measurement apparatus 2.

The operating section 19 is used for enabling the operator to perform an input operation, and may be configured by buttons, a touch panel, and the like.

The storing section 20 stores an operation program and the like, and may be configured by a storage device such as a memory, a hard disk drive, or an SD card.

The intubation controller 18 controls the sections in the intubation apparatus based on various operation signals and the like which are input by the operator through the operating section 19.

The image processing section 13, the detecting section 14, the display controller 15, and the intubation controller 18 are configured by a CPU and operation programs which cause the CPU to perform various processes, or alternatively they may be configured by digital circuits.

By contrast, the measurement apparatus 2 may include a physiological parameter calculating section 21 which is connected to the measuring section 11. The physiological parameter calculating section 21 is connected sequentially to a display controller 22 and the measurement displaying section 10. An overall storage section 23 is connected to the display controller 22. A wireless communicating section 17b is connected to the physiological parameter calculating section 21 and the overall storage section 23. Moreover, a measurement controller 24 is connected to the physiological parameter calculating section 21 and the display controller 22, and an operating section 25 and a storing section 26 are connected to the measurement controller 24.

The physiological parameter calculating section 21 calculates physiological parameter based on the measurement values which are measured by the measuring section 11. Specifically, it is known that the larger the combined amount of oxygen, the larger amount of infrared light hemoglobin in the blood absorbs. The physiological parameter calculating section 21 calculates the oxygen saturation based on the difference between the intensities of the red and infrared light beams which are received by the light detector of the measuring section 11. The physiological parameter calculating section 21 further calculates the heart rate based on variations of the intensities of the red and infrared light beams which accord to the pulsation.

The wireless communicating section 17b wirelessly communicates with the wireless communicating section 17a of the intubation apparatus 1, transmits the physiological parameter which is calculated by the physiological parameter calculating section 21, to the display controller 15, receives the composite image which is produced by the display controller 15, and outputs the composite image to the overall storage section 23.

The overall storage section 23 is configured by a memory, a hard disk drive, or the like, and sequentially stores the composite image which is produced by the display controller 15.

The display controller 22 controls the measurement displaying section 10 so as to display the physiological parameter calculated by the physiological parameter calculating section 21. The display controller 22 further controls the measurement displaying section 10 so as to display the the composite image stored in the overall storage section 23.

The operating section 25 is used for enabling the operator to perform an input operation, and may be configured by buttons, a touch panel, and the like.

The storing section 26 stores an operation program and the like, and may be configured by a storage device such as a memory, a hard disk drive, or an SD card.

The measurement controller 24 controls the sections in the intubation apparatus based on various operation signals and the like which are input by the operator from the operating section 25.

The physiological parameter calculating section 21, the display controller 22, and the measurement controller 24 are configured by a CPU and operation programs which cause the CPU to perform various processes, or alternatively they may be configured by digital circuits.

Next, the operation of the embodiment will be described.

In the intubation apparatus 1 and measurement apparatus 2 which are illustrated in FIG. 1, first, respective power supplying sections which are not illustrated are turned ON, and the sections of the intubation apparatus 1 and the measurement apparatus 2 are activated. Then, the operator attaches the measuring section 11 of the measurement apparatus 2 to the fingertip of the subject, the red light beam of the wavelength of 660 nm and the infrared light beam of the wavelength of 940 nm are emitted from the irradiator of the measuring section 11, and the light detector detects the red and infrared light beams which are transmitted through the finger tip. As illustrated in FIG. 2, a measurement signal which is produced as a result of the light detection in the light detector of the measuring section 11 is supplied from the measuring section 11 to the physiological parameter calculating section 21.

When the measurement signal which is measured by the measuring section 11 is supplied to the physiological parameter calculating section 21, the physiological parameter calculating section 21 calculates physiological parameter based on the measurement signal. Specifically, the physiological parameter calculating section 21 calculates the oxygen saturation and the heart rate as physiological parameter based on the difference between and variations of the intensities of the red and infrared light beams which are received by the measuring section 11. The oxygen saturation and heart rate which are calculated are supplied from the physiological parameter calculating section 21 to the display controller 22 and the wireless communicating section 17b.

When the oxygen saturation and heart rate which are calculated by the physiological parameter calculating section 21 are supplied to the wireless communicating section 17b, the wireless communicating section 17b outputs the oxygen saturation and the heart rate to the display controller 15 through the wireless communicating section 17a of the intubation apparatus 1.

On the other hand, when the oxygen saturation and heart rate which are calculated by the physiological parameter calculating section 21 are supplied to the display controller 22, the display controller 22 causes the oxygen saturation and the heart rate to be displayed on the measurement displaying section 10.

Figure 3:
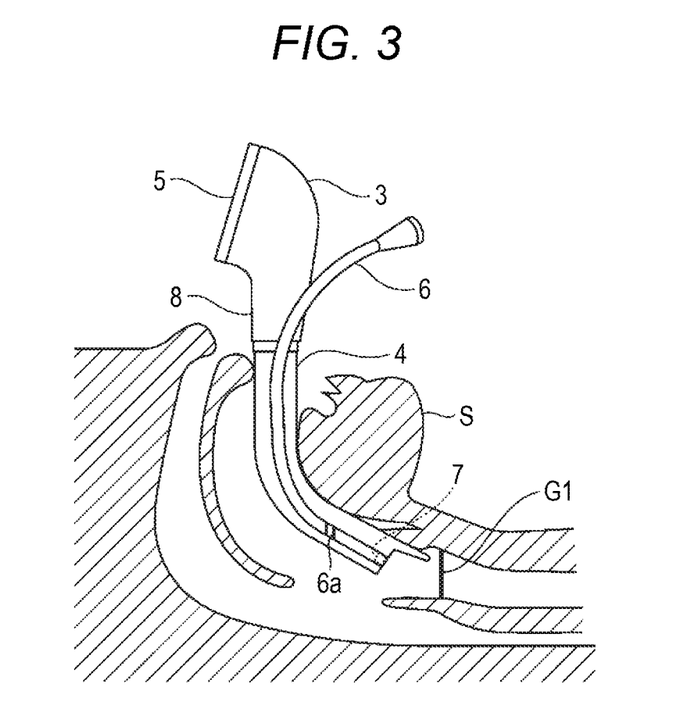
FIG. 3 is a view illustrating a manner of inserting an inserting section through the mouse of a subject.

When the oxygen saturation and the heart rate are displayed on the measurement displaying section 10 in this way, the operator who operates the intubation apparatus 1 knows the condition of the subject, and inserts the inserting section 4 through the mouth of the subject S toward the glottis G1 as illustrated in FIG. 3. At this time, an in vivo image is taken by the imaging section 7 which is placed in the vicinity of the tip end portion of the inserting section 4, and image signals of the in vivo image are sequentially supplied from the imaging section 7 to the image processing section 13. The image processing section 13 produces an in vivo image which is to be displayed on the intubation displaying section 5, based on the image signals of the in vivo image, and supplies the produced in vivo image to the detecting section 14.

When the in vivo image which is produced by the image processing section 13 is supplied to the detecting section 14, the detecting section 14 detects the glottis G1 contained in the in vivo image based on the feature amount of the glottis G1. Specifically, the detecting section 14 searches the glottis G1 contained in the in vivo image based on the feature amount of the glottis G1 which is stored in the feature amount storing section 16. Examples of the feature amount of the glottis G1 are the shape value of the vocal cords constituting the glottis G1, the chromaticity of the vocal cords, and the like. Usually, the vocal cords have a shape which arcuately extends in a fold-like manner, and exhibit a color which has an approximately white chromaticity. Namely, the vocal cords have a characteristic shape value and chromaticity. When a search process is applied to the in vivo image based on the shape value and chromaticity of the vocal cords, therefore, the glottis G1 contained in the in vivo image can be surely detected.

In addition to the feature amount of the glottis G1, preferably, the feature amount storing section 16 may store feature amounts of peripheral sites of the glottis G1, such as the epiglottis and the arytenoid cartilage. This enables the detecting section 14 to apply a search process to the in vivo image based on the feature amounts of the glottis G1 and peripheral sites of the glottis G1 which are stored in the feature amount storing section 16, and to accurately detect the glottis G1 contained in the in vivo image, based on the degree of similarity with the glottis G1 and the degree of association with the peripheral sites of the glottis G1.

The feature amount storing section 16 may further store: the feature amount of the glottis G1 which is acquired in real time from the subject S who is under measurement by the intubation apparatus; feature amounts of the glottis G1 which are acquired in past measurements; feature amounts of the glottis G1 which are acquired in past measurement from another subject; or feature amounts which are calculated by collecting these glottises G1, and which are then calculated. The feature amount of the glottis G1 is not limited to that which is measured by the intubation apparatus, and data which are collected by an external medical apparatus or the like may be used as the feature amounts.

Preferably, the feature amount storing section 16 may store the feature amounts of the glottis G1 which have various forms. For example, the feature amounts of the glottis G1 which is deformed due to a disease, those of the glottis G1 to which a shielding material such as the blood or vomitus is attached, or the like may be stored. Even in the case where the glottis G1 contained in the in vivo image has a rare shape, therefore, the detecting section 14 can surely detect the glottis G1.

The result of the detection of the glottis G1 is supplied together with the in vivo image which is taken by the imaging section 7, from the detecting section 14 to the display controller 15.

To the display controller 15, as described above, the in vivo image and the result of the detection of the glottis G1 are supplied from the detecting section 14, and the oxygen saturation and the heart rate are supplied from the physiological parameter calculating section 21 of the measurement apparatus 2. Then, the display controller 15 produces a composite image which is obtained by synthesizing the oxygen saturation and the heart rate with the in vivo image, and causes the produced composite image to be displayed on the intubation displaying section 5.

Figure 4:
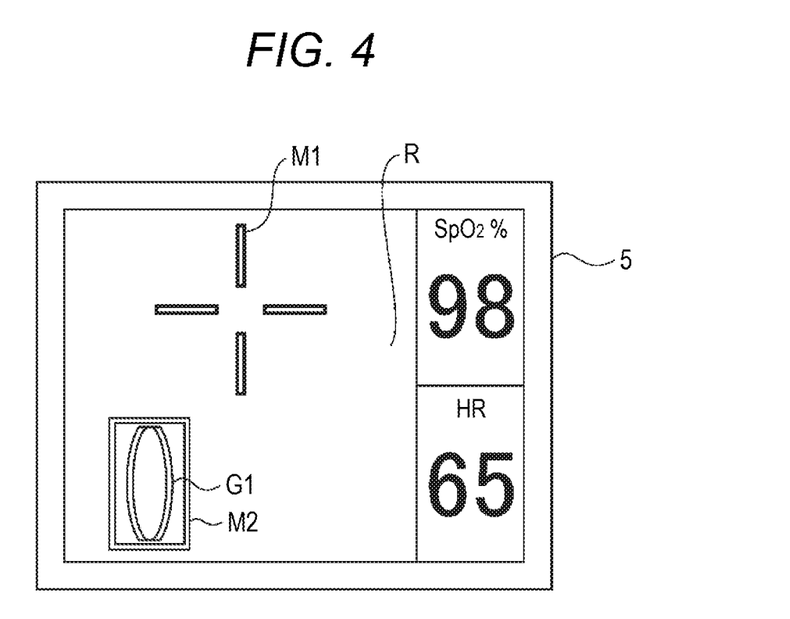
FIG. 4 is a view illustrating a manner of displaying a composite image on an intubation displaying section.

As illustrated in FIG. 4, for example, the display controller 15 can cause a composite image R in which the oxygen saturation and the heart rate are displayed in juxtaposition with the in vivo image, to be displayed on the intubation displaying section 5.

The display controller 15 causes a target mark M1 to be displayed with superimposed on the composite image R at the position corresponding to the preset advancing direction of the intubation tube 6. In the case where the glottis G1 is detected by the detecting section 14, the display controller 15 causes a site mark M2 to be displayed with superimposed on the composite image R at the position of the glottis G1 which is detected by the detecting section 14.

When the composite image R in which the physiological parameter is synthesized with the in vivo image is displayed on the intubation displaying section 5 as described above, the operator can easily know a plurality of sets of intubation information relating to intubation, without shifting the gaze from the intubation displaying section 5. While knowing the oxygen saturation and the heart rate, therefore, the operator can visually recognize the in vivo image, and safely insert the inserting section 4 toward the glottis G1. Consequently, a countermeasure against a change of the condition of the subject can be promptly taken. When the oxygen saturation and the heart rate are lowered, for example, a countermeasure in which the intubation apparatus 1 is detached from the subject, and the respiration is stabilized by using a resuscitation bag may be taken.

When only the in vivo image is displayed on the intubation displaying section 5 as in the prior art, the operator operates the inserting section 4 while gazing the in vivo image, and therefore there is a possibility that, even when the measurement apparatus 2 or the like notifies that the oxygen saturation and the heart rate are lowered, only by sound, there is a possibility that the operator does not aware of the notification. When the physiological parameter is displayed together with the in vivo image on the intubation displaying section 5, therefore, the operator can surely know the physiological parameter, and appropriately operate the inserting section 4.

The display controller 15 can produce also the composite image R in which the target mark M1 and the site mark M2 are synthesized together with the physiological parameter with the in vivo image.

As described above, the composite image R which is produced by the display controller 15 is supplied to the overall storage section 23 of the measurement apparatus 2 through the wireless communicating sections 17a, 17b, and then stored in the overall storage section 23.

Figure 5:
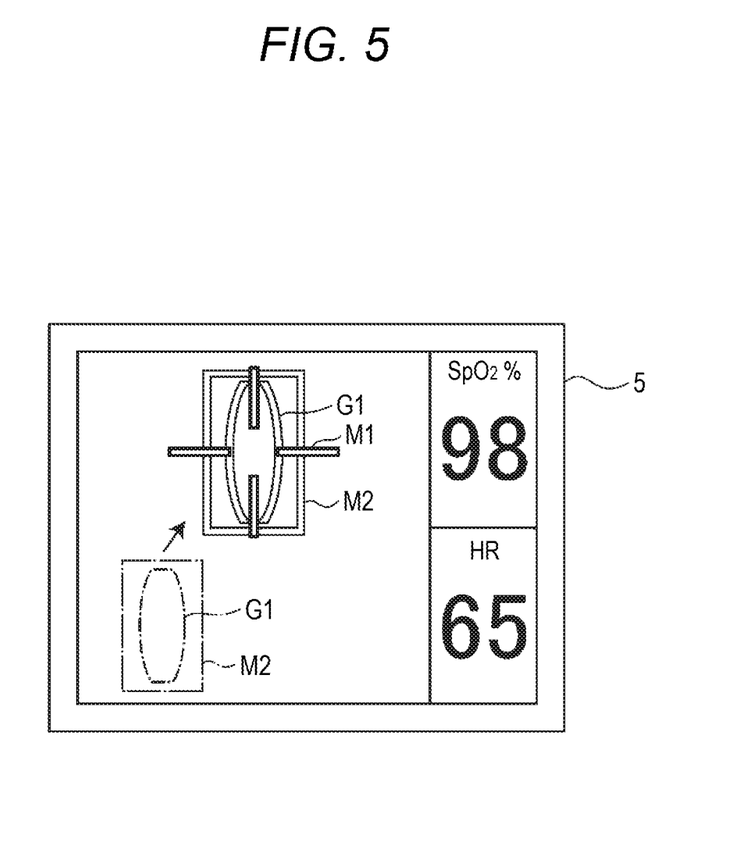
FIG. 5 is a view illustrating a manner of operating the inserting section so that a target site overlaps with a target mark.

Then, the operator operates the inserting section 4 so that the glottis G1 overlaps with the target mark M1 as illustrated in FIG. 5. As a result, the glottis G1 is located in the advancing direction of the intubation tube 6. If the operator determines that the intubation tube 6 can be inserted into the glottis G1, the intubation tube 6 is caused to forward advance, and the tip end portion of the intubation tube 6 is inserted into the glottis G1. While adjusting the insertion distance of the intubation tube 6 with using the insertion mark 6a which is disposed on the side surface of the intubation tube 6, as an index, the operator inserts the intubation tube 6 to an adequate position.

As described above, the tip end portion of the intubation tube 6 is inserted into the glottis G1 of the subject, whereby the intubation into the trachea is completed. In the case where the operator then wishes to check the state of the past intubation, the operator operates the operating section 25 of the measurement apparatus 2 so as to cause the display controller 22 to display the composite image R stored in the overall storage section 23, on the measurement displaying section 10. Therefore, the operator can easily know the in vivo image of the intubation tube, and the oxygen saturation and heart rate which correspond to the in vivo image. For example, the operator can appropriately determine whether the operation of the inserting section 4 with respect to the oxygen saturation and the heart rate is enabled or not.

According to the embodiment, the intubation displaying section 5 displays the composite image R in which the physiological parameter is synthesized with the in vivo image, the overall storage section 23 stores the composite image R which is displayed on the intubation displaying section 5, and, during and after the intubation, the operator can easily know a plurality of sets of intubation information configured by the in vivo image and physiological parameter.

Embodiment 2

Although, in above-described Embodiment 1, the overall storage section 23 stores the composite image which is displayed on the intubation displaying section 5, the overall storage section is requested to store the in vivo image and the physiological parameter in an associated manner. The information to be stored in the overall storage section is not limited to a composite image.

Figure 6:
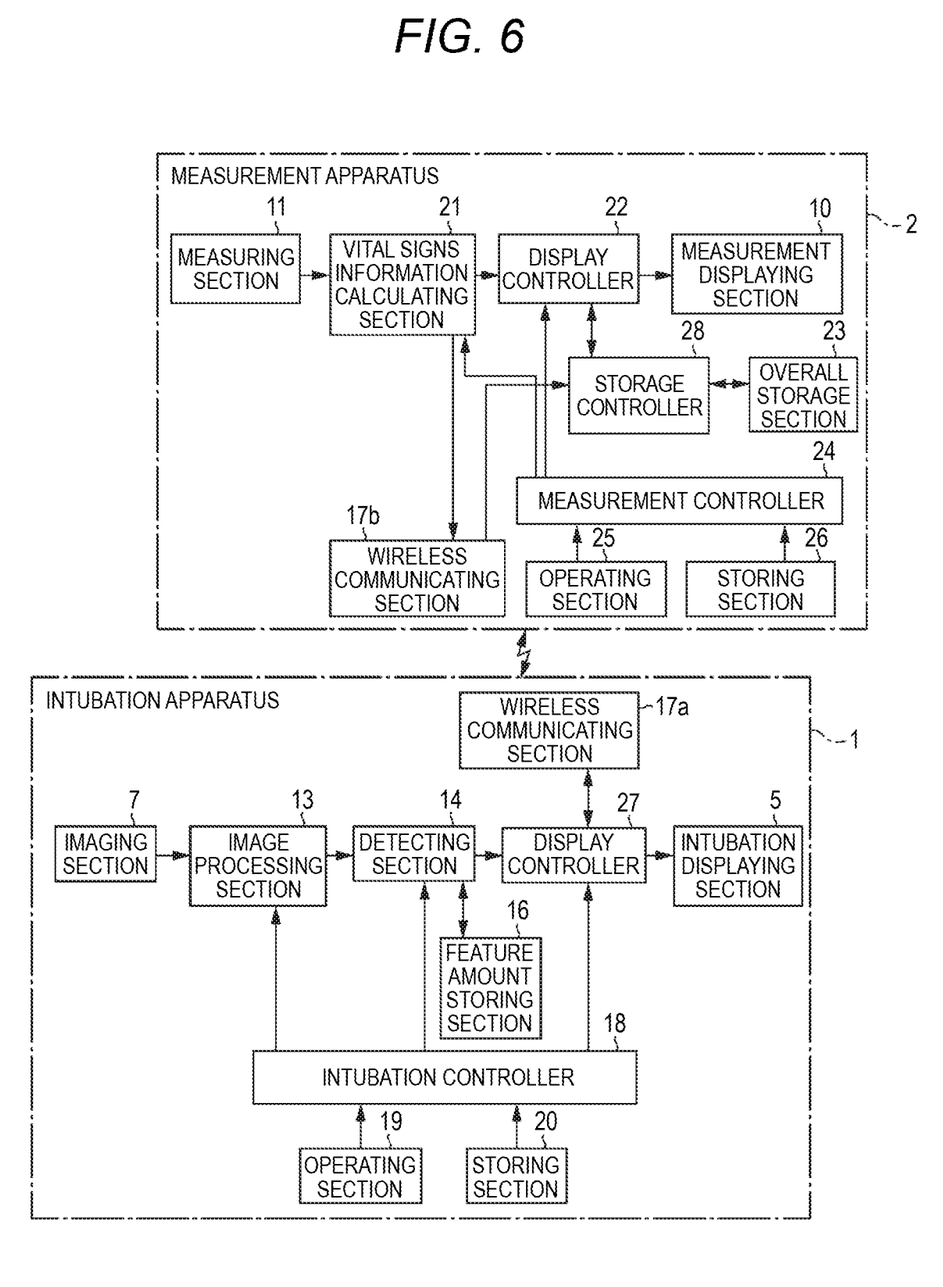
FIG. 6 is a block diagram illustrating the configurations of an intubation apparatus and measurement apparatus of Embodiment 2.

As illustrated in FIG. 6, for example, a display controller 27 may be placed in place of the display controller 15 in Embodiment 1, and a storage controller 28 may be newly placed between the wireless communicating section 17b and the overall storage section 23.

The display controller 27 causes the intubation displaying section 5 to display the physiological parameter which is measured by the measuring section 11 of the measurement apparatus 2, with superimposed on the in vivo image which is taken by the imaging section 7.

The storage controller 28 is connected to the wireless communicating section 17b, the display controller 22, and the overall storage section 23. The storage controller 28 causes the in vivo image and physiological parameter which are displayed on the intubation displaying section 5, to be sequentially stored in the overall storage section 23 in an associated manner.

According to the configuration, in the same or similar manner as Embodiment 1, the in vivo image which is taken by the imaging section 7 is supplied to the display controller 27, and the physiological parameter is supplied to the display controller from the physiological parameter calculating section 21 of the measurement apparatus 2. Then, the display controller 27 causes the physiological parameter to be displayed on the intubation displaying section 5 with superimposed on the in vivo image, and the displayed in vivo image to be supplied together with the corresponding physiological parameter to the storage controller 28 through the wireless communicating sections 17a, 17b.

When the in vivo image and the physiological parameter are supplied to the storage controller 28, the storage controller 28 sequentially stores the in vivo image and the physiological parameter in the overall storage section 23 in an associated manner. In the case where the operator wishes to check the manner of the past intubation, the operating section 25 of the measurement apparatus 2 is operated, the storage controller 28 sequentially reads an in vivo image and physiological parameter which are associated with each other, from the overall storage section 23, and the display controller 22 causes the in vivo image and the physiological parameter to be displayed on the measurement displaying section 10.

The storage controller 28 may further cause the overall storage section 23 to store the target mark M1 and the site mark M2 while being associated with the in vivo image together with the physiological parameter.

According to the embodiment, the storage controller 28 causes the overall storage section 23 to store the in vivo image and physiological parameter which are displayed on the intubation displaying section 5, in an associated manner, and therefore the display state of the physiological parameter can be freely changed with respect to the in vivo image.

Embodiment 3

In Embodiments 1 and 2 which are described above, preferably, the intubation system may include a storage controller which controls starts and stops of the storages of the in vivo image and the physiological parameter in the overall storage section 23, based on at least one of the in vivo image and the physiological parameter.

Figure 7:
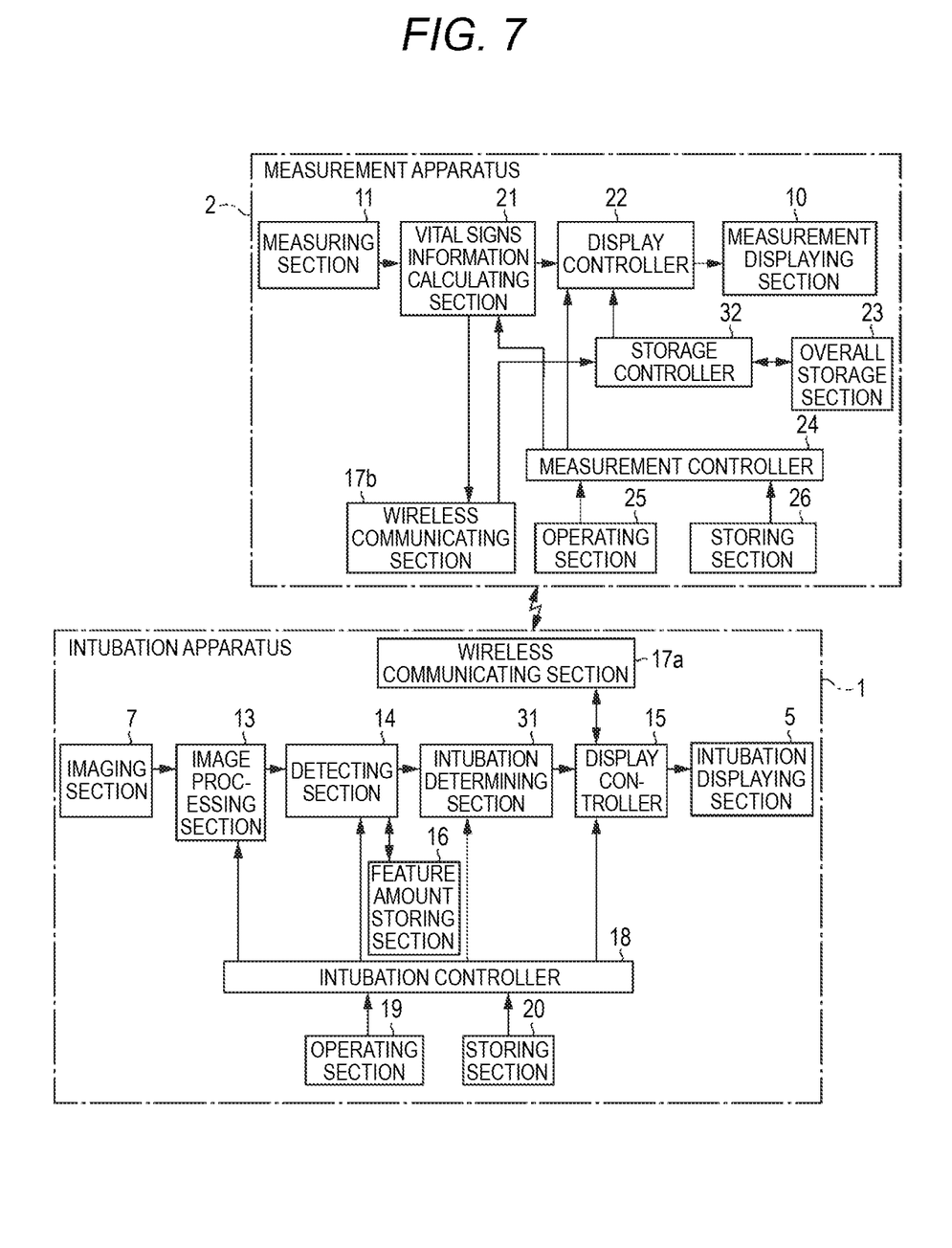
FIG. 7 is a block diagram illustrating the configurations of an intubation apparatus and measurement apparatus of Embodiment 3.

As illustrated in FIG. 7, for example, an intubation determining section 31 may be additionally placed between the detecting section 14 and the display controller 15 in Embodiment 1, and a storage controller 32 may be additionally placed between the wireless communicating section 17b and the overall storage section 23.

The intubation determining section 31 determines whether the intubation tube 6 can be inserted into the glottis G1 or not, based on the position of the glottis G1 which is detected by the detecting section 14, and the advancing direction of the intubation tube 6. Namely, the intubation determining section 31 determines whether the position of the glottis G1 which is detected by the detecting section 14 exists in the advancing direction of the intubation tube 6 or not. Here, the advancing direction of the intubation tube 6 can be set based on, for example, the forming direction of the groove portion 9 in the inserting section 4.

The storage controller 32 is connected to the wireless communicating section 17b, the display controller 22, and the overall storage section 23. If the intubation determining section 31 determines that the intubation tube 6 can be inserted into the glottis G1, the storage controller 32 causes the overall storage section 23 to start the storages of the in vivo image and the physiological parameter.

According to the configuration, in the same or similar manner as Embodiment 1, the detecting section 14 detects the glottis G1 contained in the in vivo image based on the feature amount of the glottis G1. When the position of the detected glottis G1 is supplied from the detecting section 14 to the intubation determining section 31, the intubation determining section 31 determines whether the intubation tube 6 can be inserted into the glottis G1 or not, based on the position of the glottis G1, and the advancing direction of the intubation tube 6, i.e. the position of the target mark M1.

If the position of the glottis G1 is different from the position of the target mark M1 as illustrated in FIG. 4, for example, the intubation determining section 31 determines that the intubation tube 6 cannot be inserted into the glottis G1. If the position of the glottis G1 coincides with the position of the target mark M1 as illustrated in FIG. 5, by contrast, the intubation determining section 31 determines that the intubation tube 6 can be inserted into the glottis G1. The intubation determining section 31 supplies the determination result together with the in vivo image to the display controller 15.

The display controller 15 causes the composite image R in which the physiological parameter is synthesized with the in vivo image, to be displayed on the intubation displaying section 5, and then supplies the result of the determination of the intubation determining section 31 together with the composite image R to the storage controller 32 through the wireless communicating sections 17a, 17b.

Until the intubation determining section 31 determines that the intubation tube 6 can be inserted into the glottis G1, the storage controller 32 does not cause the composite image R to be stored in the overall storage section 23, and, if the intubation determining section 31 determines that the intubation tube 6 can be inserted into the glottis G1, starts the storage of the composite image R in the overall storage section 23. The intubation determining section 31 may stop the storage of the composite image R in the overall storage section 23 at the timing such as that when the power supplying section of the intubation apparatus 1 is turned OFF, or when the insertion mark 6a formed on the intubation tube 6 is detected in the in vivo image.

This prevents the composite image R during a time period from the insertion of the inserting section 4 through the mouth of the subject to the search of the glottis G1, from being stored in the overall storage section 23, and allows only the composite image R during a time period from the start of the insertion of the intubation tube 6 to the completion of the insertion, to be stored in the overall storage section 23. When the operator wishes to check the manner of the insertion of the intubation tube 6 into the glottis G1, therefore, the operator can easily check a desired composite image R.

The storage controller 32 is not limited to the configuration in which, if the intubation determining section 31 determines that the intubation tube 6 can be inserted into the glottis G1, the storage controller 32 starts the storage. In a case such as where the detecting section 14 detects the glottis G1, or where the value of the physiological parameter reaches a threshold, for example, the storage of the composite image R may be started.

According to the embodiment, if the intubation determining section 31 determines that the intubation tube 6 can be inserted into the glottis G1, the storage controller 32 starts the storages of the in vivo image and the physiological parameter in the overall storage section 23, and therefore a desired composite image R can be easily checked.

Embodiment 4

In Embodiments 1 to 3 which are described above, preferably, the intubation system may include a notifying section which, in the case where the value of the physiological parameter that is measured by the measuring section 11 reaches a given threshold, notifies of the change of the physiological parameter.

Figure 8:
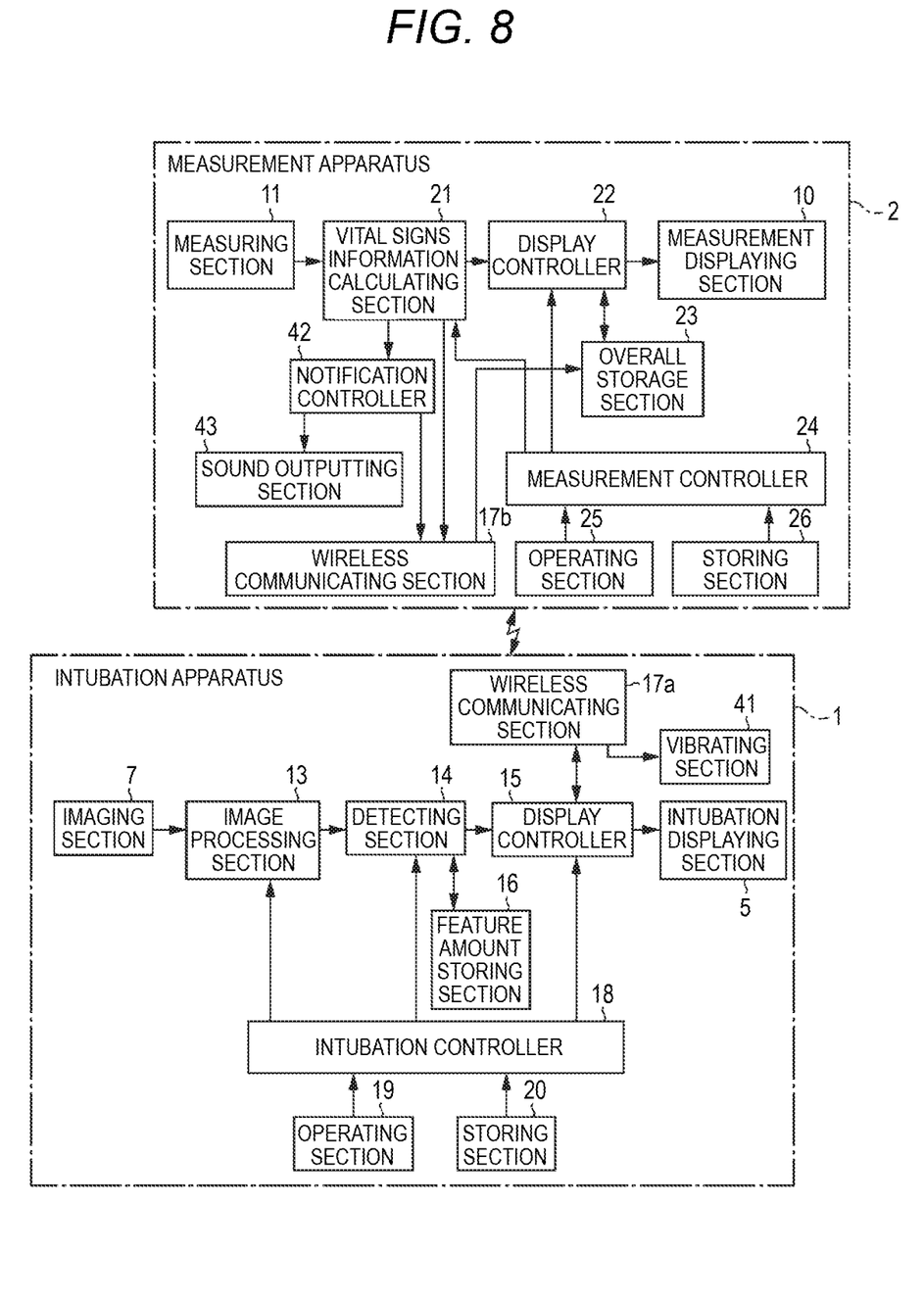
FIG. 8 is a block diagram illustrating the configurations of an intubation apparatus and measurement apparatus of Embodiment 4.

As illustrated in FIG. 8, in Embodiment 1, for example, a vibrating section 41 may be connected to the wireless communicating section 17a, a notification controller 42 and a sound outputting section 43 may be sequentially connected to the physiological parameter calculating section 21, and the notification controller 42 is further connected to the wireless communicating section 17b.

The vibrating section 41 is placed in the intubation apparatus 1, and vibrates the grasping portion 8 to notify of reductions of the oxygen saturation and the heart rate. For example, the vibrating section 41 may be configured by a vibrator.

The sound outputting section 43 is placed in the measurement apparatus 2, and outputs a warning sound to notify the operator of reductions of the oxygen saturation and the heart rate. For example, the sound outputting section 43 may be configured by a speaker.

In the case where the oxygen saturation and heart rate which are measured by the measuring section 11 are reduced to reach given thresholds, the notification controller 42 causes the vibrating section 41 to vibrate, and the sound outputting section 43 to output the warning sound.

According to the configuration, in the case where the oxygen saturation and heart rate which are calculated by the physiological parameter calculating section 21 are reduced to reach the given thresholds, the notification controller 42 causes the sound outputting section 43 to output the warning sound, and the vibrating section 41 to vibrate, through the wireless communicating sections 17a, 17b. As described above, the vibration and the warning sound are output in addition to the display of physiological parameter on the intubation displaying section 5, and therefore the operator can more surely know a change of the condition of the subject.

According to the embodiment, in the case where the value of the physiological parameter which is measured by the measuring section 11 reaches the given threshold, the notification controller 42 causes the vibrating section 41 to vibrate, and the sound outputting section 43 to output the warning sound, and therefore the operator can be more surely notified of a change of the condition of the subject.

Although, in above-described Embodiments 1 to 4, the intubation apparatus 1 is connected to one measurement apparatus, the intubation apparatus may be connected to a plurality of measurement apparatuses, and a plurality of sets of physiological parameter which are outputted respectively from the measurement apparatuses may be displayed on the intubation displaying section 5.

Although, in above-described Embodiments 1 to 4, the overall storage section 23 is placed in the measurement apparatus 2, the overall storage section is not limited to be placed in the measurement apparatus 2 as far as the in vivo image and the physiological parameter are stored in an associated manner. For example, the overall storage section may be placed in the intubation apparatus 1, or in a display device which is separated from the intubation apparatus 1 and the measurement apparatus 2.

Although, in above-described Embodiments 1 to 4, the overall storage section 23 stores the in vivo image and the physiological parameter in an associated manner, other intubation information may be further stored with associated with the in vivo image. For example, a sound inputting section such as a microphone may be placed, and ambient sounds which are input from the sound inputting section may be stored together with the physiological parameter whole being associated with the in vivo image.

Although, in above-described Embodiments 1 to 4, the display controller of the intubation apparatus 1 causes the physiological parameter to be displayed on the intubation displaying section 5 so as to overlap with the in vivo image, the presently disclosed subject matter is not limited to this as far as the physiological parameter can be displayed together with the in vivo image on the intubation displaying section 5. For example, the physiological parameter may be displayed at an interval from the in vivo image.

Although, in above-described Embodiments 1 to 4, the intubation displaying section 5 is disposed integrally with the apparatus body 3, the intubation displaying section may be placed separately from the apparatus body 3 as far as the in vivo image which is taken by the imaging section 7 can be displayed on the intubation displaying section.

Although, in above-described Embodiments 1 to 4, the in vivo image and physiological parameter which are displayed on the intubation displaying section 5 are stored in one overall storage section 23, the image and the information may be separately stored in a plurality of overall storage sections as far as they are stored in an associated manner. For example, two overall storage sections may be placed, the in vivo image is stored in one of the overall storage sections, and the physiological parameter associated with the in vivo image may be stored in the other overall storage section. In this case, the in vivo image and the physiological parameter may be stored while being associated with the time when the image and the information are displayed on the intubation displaying section 5.

What is claimed is:

1. An intubation system comprising:
a measurement apparatus that measures a physiological parameter of a subject by at least one or more of an irradiator or a detector;
an intubation apparatus that includes a sensor placed in a vicinity of a tip end portion of an inserting section to be inserted from a mouth of the subject toward a target site;
a display device that is disposed integrally with the intubation apparatus and is connected to the sensor and the at least one or more of the irradiator or the detector, and is configured to display an in vivo image that is taken by the sensor along with the physiological parameter that is measured by the at least one or more of the irradiator or the detector; and
a memory that is configured to store the in vivo image and the physiological parameter that are displayed by the display device, wherein:
the display device is further configured to display a composite image obtained by synthesizing the physiological parameter with the in vivo image,
the memory is further configured to store the composite image, and
the memory is further configured to start storage of the composite image obtained by synthesizing the physiological parameter with the in vivo image based on whether or not an intubation tube is inserted into a glottis.

2. The intubation system according to claim 1 further comprising:
at least one of:
a vibrator of the intubation apparatus that vibrates a grasping portion of the intubation apparatus to be grasped by an operator;
a speaker that is configured to output a warning sound in the at least one or more of the irradiator or the detector; and
a notification controller that causes at least one of the vibrator and the speaker to operate when a value of the physiological parameter that is measured by the at least one or more of the irradiator or the detector reaches a given threshold.

3. The intubation system according to claim 1, wherein the memory is disposed in the measurement apparatus,
the measurement apparatus includes a second display device that is configured to display the physiological parameter that is measured by the at least one or more of the irradiator or the detector, and displays the in vivo image stored in the memory together with corresponding physiological parameter on the second display device.

4. The intubation system according to claim 1, wherein the display device is further configured to display a target mark at a first position in first direction of an intubation tube and superimposed on the composite image, and display a site mark at a second position of the glottis and superimposed on the composite image.

5. The intubation system according to claim 1, wherein a plurality of sets of intubation information relating to intubation of the subject by the intubation system are obtained by the display device based on the display of the composite image.

6. The intubation system according to claim 1, wherein the intubation apparatus is configured to display a determination result of whether or not the intubation tube is inserted into the glottis, the determination result being based on a position of the glottis relative to a position of a target mark.

7. The intubation system according to claim 1, wherein the in vivo image comprises a larynx image.

8. An intubation system comprising:
a measurement apparatus that measures a physiological parameter of a subject by at least one or more of an irradiator or a detector;
an intubation apparatus that includes a sensor placed in a vicinity of a tip end portion of an inserting section to be inserted from a mouth of the subject toward a target site;
a display device that is disposed integrally with from the intubation apparatus and is connected to the sensor and the at least one or more of the irradiator or the detector to display an in vivo image that is taken by the sensor along with the physiological parameter that is measured by the at least one or more of the irradiator or the detector;
a memory that is configured to store the in vivo image and the physiological parameter; and
a storage controller that controls a start timing of storing the in vivo image that is taken by the sensor and the physiological parameter that is measured by the at least one or more of the irradiator or the detector, in the memory based on at least one of the in vivo image and the physiological parameter.

9. The intubation system according to claim 8, wherein the intubation apparatus includes:
a processor that is configured to detect a target site, from the in vivo image that is taken by the sensor, based on a feature amount of the target site that is preset; and
an intubation determining section that determines whether an intubation tube is insertable into the target site or not, based on a position of the target site which is detected by the processor, and an advancing direction of the intubation tube which is disposed so as to be advanceable and retractable along the inserting section, and, wherein when the intubation determining section determines that the intubation tube is insertable into the target site, the storage controller causes the memory to start storing the in vivo image and the physiological parameter.

* * * * *